US00PP10840P

United States Patent [19]

Simmons et al.

[11] Patent Number: Plant 10,840

[45] Date of Patent: Mar. 30, 1999

[54] APPLE TREE NAMED 'SIMMONS GALA'

[75] Inventors: Daniel E. Simmons; Daniel E. Simmons, Jr., both of Rogers; Paul A. Simmons, East Palestine, all of Ohio

[73] Assignee: Peace Valley Orchards, Rogers, Ohio

[21] Appl. No.: 708,775

[22] Filed: Sep. 5, 1996

[51] Int. Cl.[6] ..... A01H 5/00

[52] U.S. Cl. ..... Plt./34.1

[58] Field of Search ..... Plt./34.1

[56] References Cited

U.S. PATENT DOCUMENTS

| | | | |
|---|---|---|---|
| P.P. 3,637 | 10/1974 | McKenzie | Plt./34.1 |
| P.P. 4,121 | 10/1977 | Ten Hove | Plt./34.1 |
| P.P. 6,172 | 5/1988 | Creech | Plt./34.1 |
| P.P. 6,955 | 8/1989 | Kiddle | Plt./34.1 |
| P.P. 7,396 | 12/1990 | Cooper | Plt./34.1 |
| P.P. 7,589 | 7/1991 | Fulford | Plt./34.1 |
| P.P. 8,621 | 3/1994 | Olsen et al. | Plt./34.1 |
| P.P. 8,673 | 4/1994 | Waliser | Plt./34.1 |
| P.P. 8,720 | 5/1994 | Hill | Plt./34.1 |
| P.P. 9,681 | 11/1996 | Olsen et al. | Plt./34.1 |
| P.P. 10,114 | 11/1997 | Gale | Plt./34.1 |

*Primary Examiner*—Howard J. Locker
*Attorney, Agent, or Firm*—Flynn, Thiel, Boutell & Tanis, P.C.

[57] ABSTRACT

The new and distinct cultivar of apple tree originated as a limb mutation of the 'Imperial Gala' variety. The fruit of this cultivar is distinguished by its early coloring, full deep rich red coloration, and distinctive strong red striping that covers the entire fruit.

6 Drawing Sheets

FIELD OF THE INVENTION

The present invention relates to apple trees and more specifically to a new and distinct variety of apple tree which has a fruit that has an early bright red color and distinctive red striping that covers the entire fruit.

BACKGROUND OF THE INVENTION

The new variety of apple is of the Gala-type.

SUMMARY OF THE INVENTION

This new variety, which is a mutation of the Imperial Gala variety, was found as a limb mutation among trees growing at Peace Valley Orchard in Rogers, Ohio. We were attracted to the new variety because of the early and much brighter red color and distinctive red striping that covers the entire fruit. The new variety has been asexually reproduced by budding at Peace Valley Orchards, Rogers, Ohio. The first generation was budded on Aug. 20, 1994. Asexual propagation shows that the unique combination of characteristics and distinctive color come true to form and are established and transmitted through succeeding propagations.

The fruit of the apple tree of the new variety exhibits an attractive appearance and, unlike the parent variety, possesses an overall full deep rich red color with a strong stripe. This coloration and striping is present over the entire surface of the fruit and develops at least 21 days earlier than the parent. This new variety has been named the 'Simmons Gala' variety.

The new variety can be distinguished from the 'Gale Gala' cultivar (U.S. Plant Pat. No. 10,114) by the absence of any red coloration on the leaf midvein. The 'Gale Gala' cultivar exhibits red color on almost the entire length of the leaf's midvein while the new variety is completely green. The new variety can also be distinguished from the 'Gale Gala' cultivar by the differences in flower petal formation. The new variety has large, ruffled, almost white petals with little pink coloration. The 'Gale Gala' has smaller, unruffled petals with much more pink coloration.

The new cultivar of the present invention can be distinguished from other cultivars of Gala-type apple trees such as the Kidd's D-8 cultivar (U.S. Plant Pat. No. 3,637), the Waliser cultivar (U.S. Plant Pat. No. 8,673), the Kiddle cultivar (U.S. Plant Pat. No. 6,955), the Obragala cultivar (U.S. Plant Pat. No. 8,621), the Creech cultivar (U.S. Plant Pat. No. 6,172), the Tenroy cultivar (U.S. Plant Pat. No. 4,121), the Cooper cultivar (U.S. Plant Pat. No. 7,396) and the Olsentwo cultivar (U.S. Plant Pat. No. 9,681) in view of the combination of characteristics discussed herein. The new variety can be distinguished from the Kidd's D-8 cultivar by the striping and high percentage of color on the new variety. The new variety also develops significant fruit color 21 days before Kidd's D-8. The new variety can be compared to and distinguished from its parent, 'Imperial Gala', as while both cultivars show a higher percentage of red coloration and striped pattern on the fruits than 'Kidd's D-8', the new variety has much higher coloration of the fruit, and shows significant fruit color 21 days earlier than does 'Imperial Gala'.

The new variety can be distinguished from the Tenroy cultivar by the percentage of striping on its fruits. The new variety exhibits bright, prominent red striping in 100% of ripened fruits while the ripened fruits of the Tenroy cultivar exhibits "striping in some fruit". The new variety develops significant fruit color 21 days before the Tenroy cultivar.

The new variety can be distinguished from the Waliser cultivar by the size of the stripes. The new variety exhibits a broad, bright red striping pattern while the Waliser cultivar exhibits a "pinstriping" pattern. The new variety develops significant fruit color 11 days before the Waliser cultivar.

The new variety can be distinguished from the Obragala cultivar by the type of coloration of the fruits. The new variety has a strong, distinctive, bright red stripe while the Obragala cultivar has a blush coloration. The new variety also develops significant fruit color 11 days before the Obragala cultivar and ripens two to four days later.

The new variety can be distinguished from the Creech cultivar by its ripening date which is 10 days later and by the new variety's development of significant fruit color 21 days before the Creech cultivar. The new variety exhibits a striped pattern of fruit coloration while the Creech cultivar is a blush.

The new variety can be distinguished from the Kiddle cultivar by the prominence of the stripe on the fruits. The new variety exhibits a very prominent, all over striping pattern while the Kiddle cultivar exhibits an "indistinct stripe" pattern on its fruits. The new variety develops significant fruit color 19 days before the Kiddle cultivar.

The new variety can be distinguished from the Olsentwo cultivar by the timing of color development. The new variety develops significant fruit color 11 days before the Olsentwo cultivar.

The new variety can be distinguished from the Cooper cultivar by the absence of a compact spurring tendency. The new variety also develops significant fruit color 19 days before the Cooper cultivar.

A search for fruiting examples of the Applewaites cultivar (U.S. Plant Pat. No. 8,720) in the United States proved unsuccessful. A comparison of the patent shows that the new variety differs from Applewaites by the presence of a stripe and the development of significant fruit color approximately 19 days before Applewaites.

Development of early, significant coloration of the fruits is a very desirable commercial attribute for a new apple variety. This allows the grower to harvest the fruit at the optimum time for handling, shipping and storage without having to wait for marketable color to develop. The color development of the new variety distinguishes it from all other previously patented Gala cultivars. The new variety develops significant fruit color from 10 to 21 days earlier than the other cultivars as shown in the chart below. This color development occurs first as a striping pattern and fills in rapidly to a 90 to 100% soft red color, quickly changing to a full, bright red while the fruits of other varieties are greenish yellow with a pink cheek.

This data was obtained from grower comparisons of the previously mentioned Gala varieties in the States of Michigan, Ohio and Washington. While harvest times differ in these sites, the timing of the onset of coloration in comparison to the harvest date is comparable. The determination of commercial maturity as referred to in this application is the determination by the grower through experience, color development, and starch and sugar content that the particular cultivar is mature for picking. The comparative color development of various Gala varieties is shown schematically in the following chart:

Color Development Comparison of Patented GALA Cultivars

| Simmons | Obragala<br>Waliser<br>Olsentwo | Kiddle<br>Cooper | Kidd's D-8<br>Tenroy<br>Creech<br>Fulford<br>Applewaite |
|---|---|---|---|
| +21 days | +10 days | +2 days | 0 days |

BRIEF DESCRIPTION OF THE DRAWINGS

The accompanying photographs show typical specimens of the new variety as depicted in color as nearly true as it is reasonably possible to make the same in color illustrations of this character. These specimens were obtained at Peace Valley Orchards, Rogers, Ohio, 44455.

DETAILED DESCRIPTION OF THE INVENTION

Figure 1:
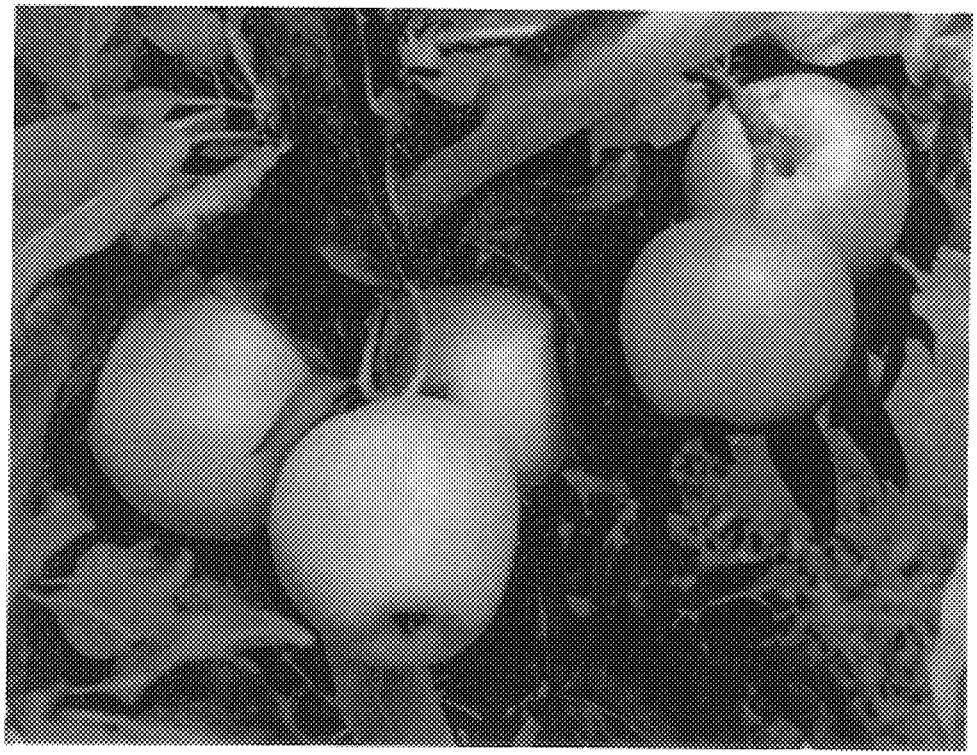
FIG. 1 illustrates two specimens of the new variety on the right and three specimens of the parent on the left. This picture shows the original limb mutation on the same tree and was taken 18 days before the fruits were mature. It shows the extremely early color development of the new variety in comparison to the parent.
Figure 2:
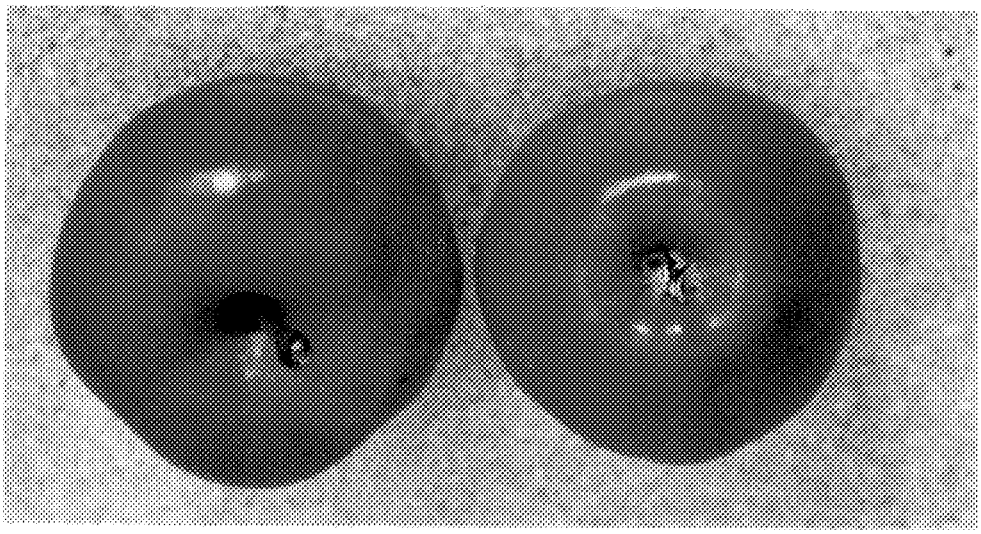
FIG. 2 shows the calyx and stem ends of the fruit of the new cultivar at commercial maturity.
Figure 3:
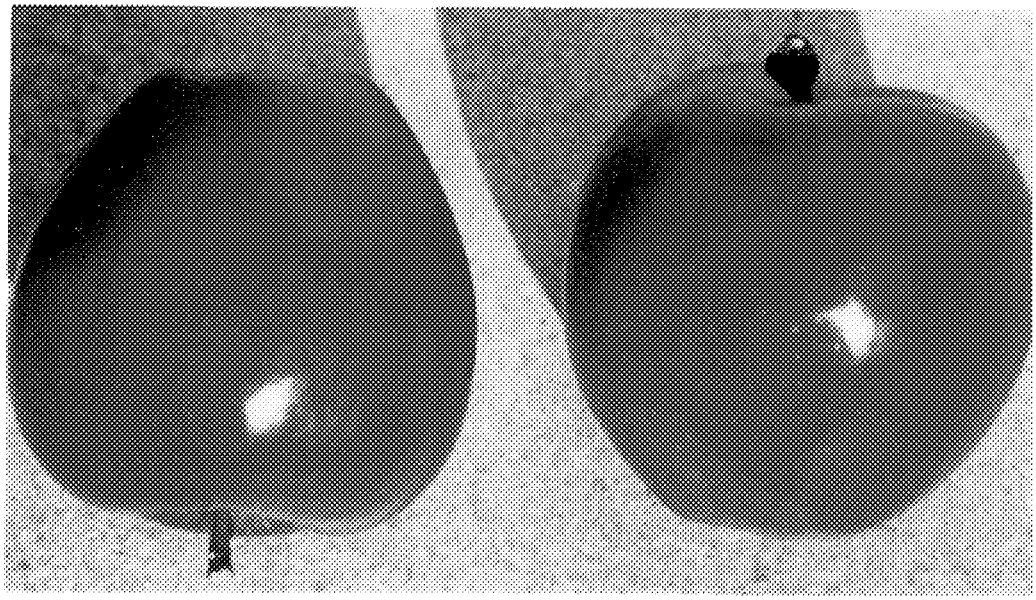
FIG. 3 shows side views of the fruit of the new cultivar at commercial maturity.
Figure 4:
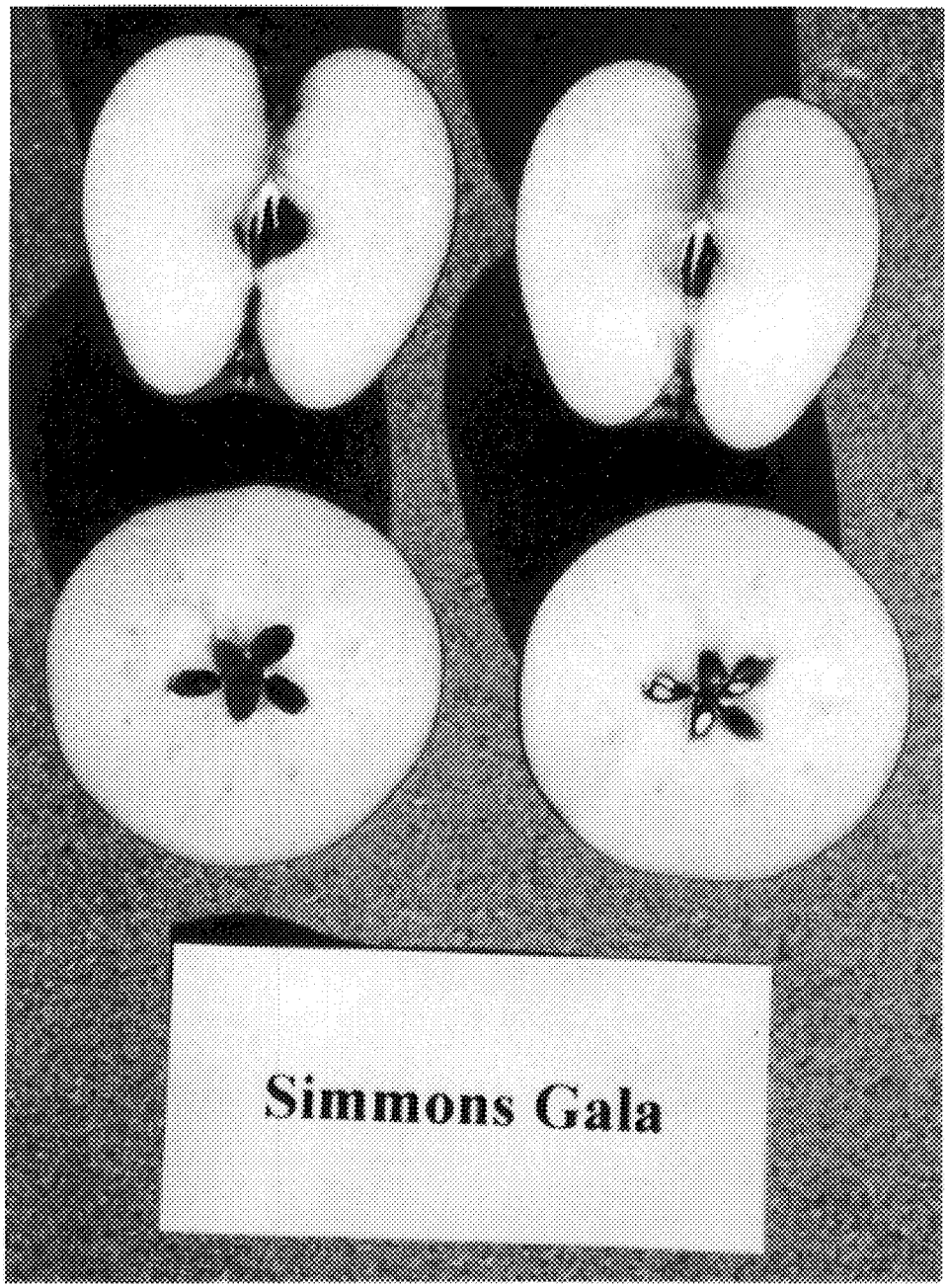
FIG. 4 illustrates internal cross sections of the fruit of the new cultivar at commercial maturity.
Figure 5:
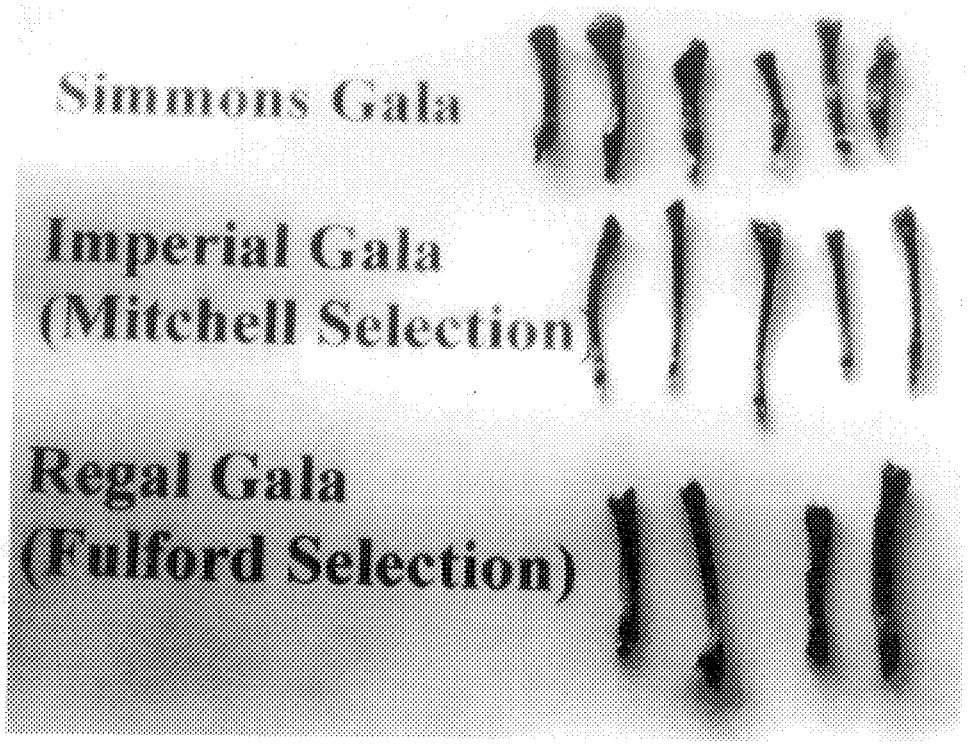
FIG. 5. illustrates the differences in the stem shape and size between the new cultivar, 'Imperial Gala', and 'Regal Gala', showing the pronounced clubbing at the distal end and the prominent, rounded swelling at the base.
Figure 6:
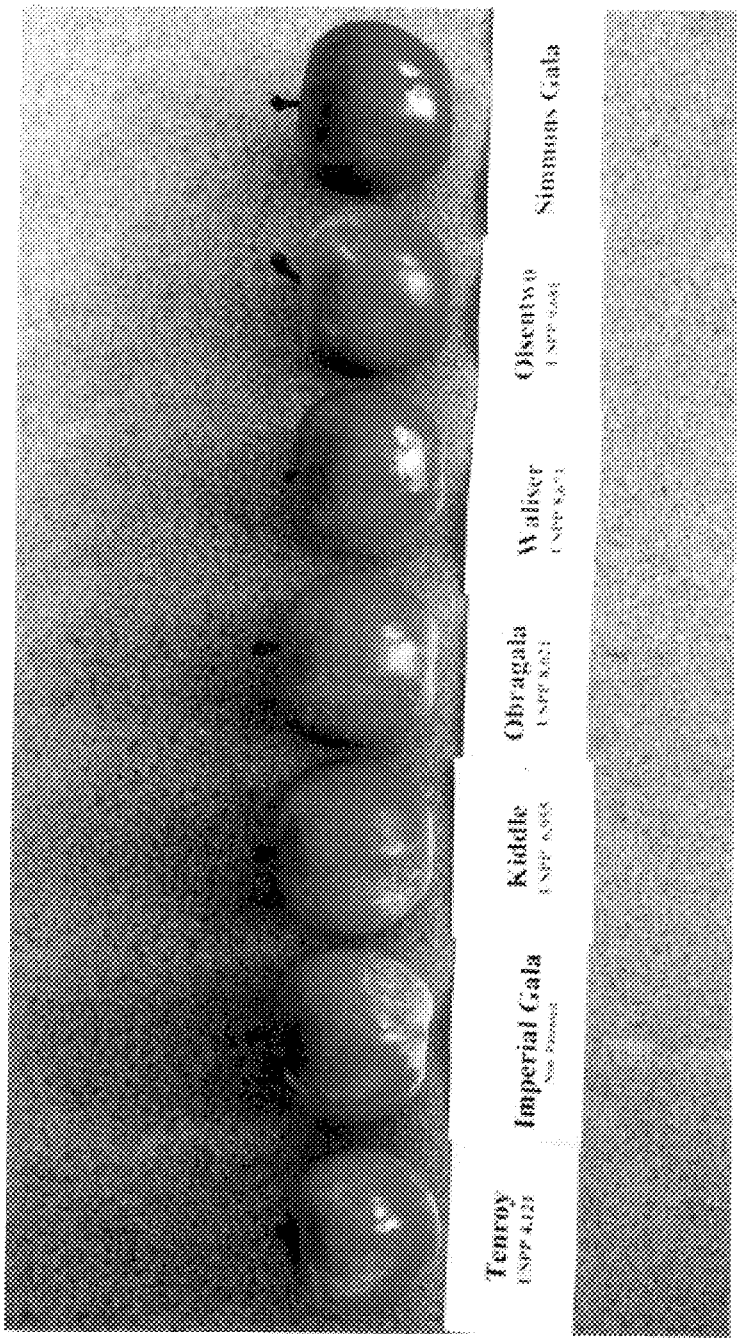
FIG. 6 illustrates fruits of the new cultivar and other comparable 'Gala' cultivars at commercial maturity, illustrating the differences in coloration and striping patterns. Specimens for this picture were obtained from Peace Valley Orchards and other mid-western orchards with very similar commercial maturity dates.
Figure 7:
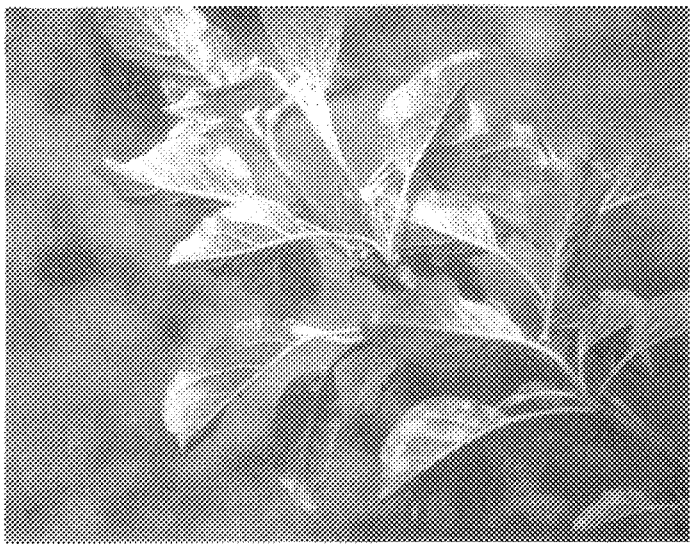
FIG. 7 illustrates the underside of the foliage of the new cultivar, showing the completely green midveins.
Figure 8:
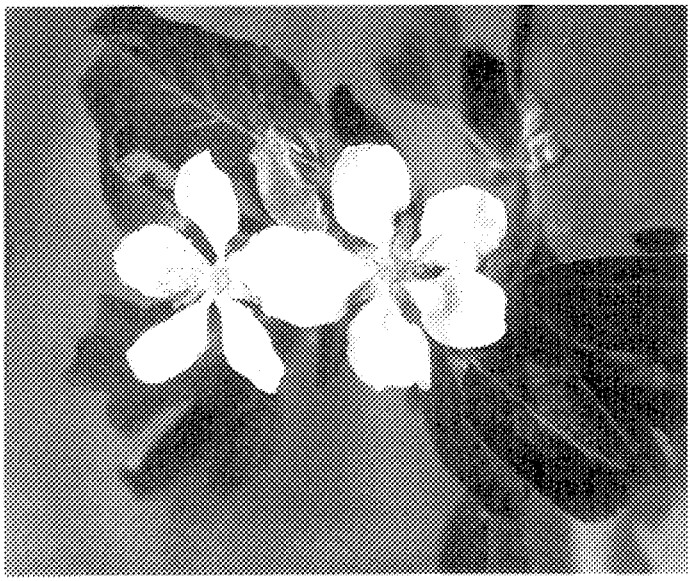
FIG. 8 illustrates the blossoms of the new cultivar.

Locality where grown and observed: Rogers, Ohio.

Dates of first and last pickings on normal years: About August 27 and September 4 in Rogers, Ohio.

Tree: Medium, vigorous; spreading; rounded; hardy; productive; regular bearing. The pruning and thinning requirements are the same as the parent and Kidd's D-8. The new variety bears fruit in the same manner as the parent and Kidd's D-8.

Trunk: Medium; smooth; Royal Horticultural Society Color Chart, Fan 4, Gray Group, 201B.

Branches: Medium thick, smooth, Royal Horticultural Society Color Chart, Fan 4, Brown group, 200B. Lenticels: Prominent; numerous; medium large. Essentially the same as the parent and Kidd's D-8.

Leaves: Length, 4", Width, 2¼", Large; oval; abruptly pointed; Leaves and petioles are essentially the same as the parent and Kidd's D-8; The Royal Horticultural Society Colour Chart, Fan 3, Yellow-green group, 147A. Margin: Crenate. Stipules similar to other Galas. Leaf stems and mid-vein or veins on the bottom surfaces of the leaves are green.

Flowers: Early mid-season bloom with a long bloom period, Large ruffled petals with very little pink coloration.

*Date of bloom.*—About May 8th to 15th, in Rogers, Ohio.

*Pollination requirements.*—Any diploid variety in the same season except pollen from golden delicious or any other Gala sport.

Fruit: Maturity when described, eating ripe. Maturity date is the same as the parent and Kidd's D-8.

*Size.*—Uniform; axial diameter, 2⅞", transverse diameter, 2¾", form, globose.

*Cavity.*—Symmetrical, abrupt at base; apex acuminate; depth, ¾", breadth ¾".

*Markings.*—None.

*Basin.*—Symmetrical; rounded, wide, breadth ¾", depth, ½", markings, none.

Stem: Length, 1¼", breadth, 1/16", stout; clubbed at head; prominent rounded swelling at base.

Calyx: Closed.

*Segments.*—Broadly lanceolate; reflexed from base at apex; approximate.

*Outer surface.*—pubescent.

*Inner surface.*—pubescent.

Eye: Closed.

Skin: Thin; smooth; waxed; glossy.

*Color of dots.*—Royal Horticultural Society Colour Chart, Fan 1, yellow group, 10 A.

*Ground color.*—Royal Horticultural Society Colour Chart, Fan 1, yellow-orange group, 18 A.

*Color markings.*—The fruits are 100% bright glossy, red with prominent lenticels. The entire fruit is striped with a strong, broad stripe averaging 2/16 to 3/16ths of an inch in width. The stripe runs the entire length of the fruit. The stripe alternates dark red and lighter red in a pleasing, attractive pattern. The ground color is dark glossy red with lighter areas around the lenticels. The fruit is entirely colored from the calyx to the stem end.

*Color of markings.*—Royal Horticultural Society Colour Chart, Fan 1, red group, 46 A.

*General color effect.*—Bright prominent red stripe over 100% of fruit, background clear yellow, very attractive appearance.

Flesh: Juicy; satiny; Color: Royal Horticultural Society Colour Chart, Fan 1, yellow-orange group, 19 D.

*Texture.*—Firm; tender; fine; crisp.

*Flavor.*—Sweet, aromatic.

*Quality.*—best.

Core:

*Bundle area.*—Small; oblate.

*Bundles.*—Inconspicuous; in one whorl.

*Core lines.*—Clasping; indistinct.

*Calyx-tube.*—Funnelform; glabrous toward base.

*Stem of funnel.*—Long.

*Depth of tube to shoulder.*—¼".

*Entire depth.*—⅝".

*Styles.*—Present.

*Stamens.*—Present, one distinctive whorl.

*Auxiliary cavity.*—Present.

*Seed cells.*—Axile, open.

*Cell walls.*—*Medium thin.*

*Length.*—½".

*Breadth.*—¼".

*Longitudinal section.*—Orbicular, obtuse at apex.

*Surface.*—Smooth.

*Cross section.*—Broad.

Seeds:

*Number perfect*—6 to 10.

*Number in one cell.*—2.

*Length.*—⅜".

*Breadth.*—3/16".

*Color.*—*The Royal Horticultural Society Colour Chart, Fan* 4, Brown group, 200 B.

Use: Market; dessert.

Keeping quality: Good; 3 months is common storage, 7 months in controlled atmosphere.

Resistance to:

*Insects.*—Good.

*Diseases.*—Good, susceptible to mildew, scab and fire-blight. Generally free of skin russet. Somewhat susceptible to scarf-skin.

What is claimed is:

1. A new and distinct cultivar of apple tree, substantially as herein shown and described.

* * * * *